United States Patent
Watterson et al.

[11] Patent Number: 5,879,626
[45] Date of Patent: Mar. 9, 1999

[54] PHOTOELECTRIC SENSOR HAVING DUST REMOVAL APPARATUS

[75] Inventors: Richard L. Watterson, Antrim, N.H.; David R. Hagemeier, Andover, Mass.; James J. Boschuetz, Jr., Wausau, Wis.

[73] Assignee: Allen-Bradley Company, LLC, Milwaukee, Wis.

[21] Appl. No.: 902,707
[22] Filed: Jul. 30, 1997
[51] Int. Cl.⁶ .................................. G02B 7/00
[52] U.S. Cl. .................. 422/62; 422/82.05; 359/509
[58] Field of Search ............... 359/509; 134/37; 422/82.05, 62

[56] References Cited

U.S. PATENT DOCUMENTS

| | | | |
|---|---|---|---|
| 2,856,542 | 10/1958 | McPheeters | 359/509 |
| 3,744,873 | 7/1973 | Jamison | 359/509 |
| 4,240,691 | 12/1980 | Holmqvist et al. | 359/509 |
| 4,658,113 | 4/1987 | Vingerling | 359/509 |

*Primary Examiner*—Jeffery Snay
*Attorney, Agent, or Firm*—David G. Luettgen; John M. Miller; John J. Horn

[57] ABSTRACT

A photoelectric sensor has its own cleaning system which accommodates different possibilities for mounting the photoelectric sensor, so that it is no longer necessary to custom design cleaning systems. The photoelectric sensor includes an optical lens and a cleaning device which cleans the optical lens. The cleaning device further includes a fluid chamber coupled to a source of fluid, and a fluid dispenser in fluid communication with the fluid chamber and disposed adjacent the optical lens. The fluid dispenser is operative to dispense fluid on the optical lens to clean the optical lens. In a preferred embodiment, the cleaning system uses a pulse of air to remove dust from the optical lens of the photoelectric sensor.

20 Claims, 4 Drawing Sheets

PHOTOELECTRIC SENSOR HAVING DUST REMOVAL APPARATUS

1. Field of the Invention

This invention relates to photoelectric sensors, and more particularly relates to a photoelectric sensor having an apparatus which removes dust and other types of dirt from a lens thereof.

2. Description of Related Art

Photoelectric sensors are known in the field of industrial controls for sensing objects within the field of view of the photoelectric sensor. Photoelectric sensors generally include a source and a detector, and can operate according to different various modes of operation, including transmitted beam sensing modes, retroreflective sensing modes and proximity (or diffuse) sensing modes. For example, in a proximity sensing mode, the source emits a light beam which is detected by the detector if an object is present to reflect the light beam. When no object is present, the light beam is not reflected and therefore is not detected by the detector. Whether the detector detects a reflected light beam thus provides an indication whether an object is present.

Photoelectric sensors are used in industrial facilities which are often dusty or otherwise dirty. For example, if factory operations include wood cutting, saw dust is generated which fills the air and which eventually settles on the lenses of the source and the detector. The presence of dust on the lenses of the source and detector is problematic, because it degrades the performance of the photoelectric sensor.

Various systems and procedures have been devised for periodically cleaning industrial facilities such as factories. For example, factories undergo periodic washdowns in which the entire factory is cleaned, including any photoelectric sensors and components thereof. In factories which are particularly dusty, a limited number of systems have also been specially developed for cleaning photoelectric sensors in between the periodic washdowns. For example, some factories have installed air blower systems which periodically blow air on the lenses of photoelectric sensors to remove dust therefrom. These systems are separate from the photoelectric sensor and are mounted to nearby factory equipment.

The drawback of these specially developed systems is that they are costly. Each system must be custom-designed to accommodate each factory and each photoelectric sensor within each factory. The location and placement of photoelectric sensors within factories is always different and is dictated by the unique sensing needs of the factory. Photoelectric sensors may be placed so as to have any given orientation (up, down, sideways, or at an angle). No cleaning system has ever been provided which accommodates different possibilities for mounting a photoelectric sensor in different locations and orientations.

SUMMARY OF THE INVENTION

To overcome these drawbacks of the prior art, the present invention provides a photoelectric sensor having its own cleaning system which accommodates different possibilities for mounting the photoelectric sensor, so that it is no longer necessary to custom design cleaning systems.

Specifically, a photoelectric sensor according to the present invention comprises an optical lens and a cleaning device which cleans the optical lens. The cleaning device further includes a fluid chamber coupled to a source of fluid, and a fluid dispenser in fluid communication with the fluid chamber and disposed adjacent the optical lens. The fluid can be a gas (e.g., air) and/or liquid. The fluid dispenser is operative to dispense fluid on the optical lens to clean the optical lens.

In a more preferred embodiment, a photoelectric sensor according to the present invention comprises a housing, an optical lens, and a cleaning device which removes dust from the optical lens. The cleaning device is an attachment which is non-integrally formed with the housing and which attaches to the housing. The attachment further includes a principal section and an insert which is inserted into the principal section.

The principal section further includes a base, a lateral support, and first and second retainers. The first and second retainers attach the cleaning device to first and second sides of the housing of the photoelectric sensor. The base, the lateral support and the first and second retainers define a window which permits an unobstructed field of view for the photoelectric sensor.

The insert and the principal section combine to form an air chamber and an air dispenser. The air chamber is coupled to a source of compressed air. The air dispenser is in fluid communication with the air chamber and comprises a slotted orifice formed between a lip of the base and a lip of the insert. The resulting cleaning device attaches to the housing of the photoelectric sensor such that the dispenser is disposed adjacent the optical lens and is operative to dispense air on the optical lens to dislodge dust from the optical lens.

The photoelectric sensor is coupled to an industrial controller, which in turn is coupled to a valve which controls the flow of air from the source of compressed air to the cleaning device. The industrial controller is thereby able to control the cleaning of the optical lens.

The present invention also provides a method of cleaning an optical lens of a photoelectric sensor. The method according to the present invention comprises the steps of generating a fluid flow, delivering the fluid flow to the photoelectric sensor, channeling the fluid flow through a fluid channel disposed within the photoelectric sensor, and then directing the fluid flow at the optical lens from the fluid channel.

Advantageously, the present invention provides a cleaning system which accommodates different possibilities of mounting a photoelectric sensor in different locations and orientations. There is no need to mount a separate specially developed cleaning system to nearby factory equipment, because the cleaning device is a part of the photoelectric sensor. Furthermore, the present invention facilitates factory changes and upgrades because remounting a photoelectric sensor that is equipped with the invention does not require remounting its cleaning device. Finally, since the cleaning device is not integrally formed with the main housing but rather attaches to the sensor housing, the same sensor housing may be used both for photoelectric sensors which incorporate a cleaning device and for those which do not incorporate a cleaning device.

Other objects, features, and advantages of the present invention will become apparent to those skilled in the art from the following detailed description and accompanying drawings. It should be understood, however, that the detailed description and specific examples, while indicating preferred embodiments of the present invention, are given by way of illustration and not limitation. Many modifications and changes within the scope of the present invention may be made without departing from the spirit thereof, and the invention includes all such modifications.

BRIEF DESCRIPTION OF THE DRAWINGS

A preferred exemplary embodiment of the invention is illustrated in the accompanying drawings in which like reference numerals represent like parts throughout, and in which.

DETAILED DESCRIPTION OF THE PREFERRED EMBODIMENT

Figure 1:
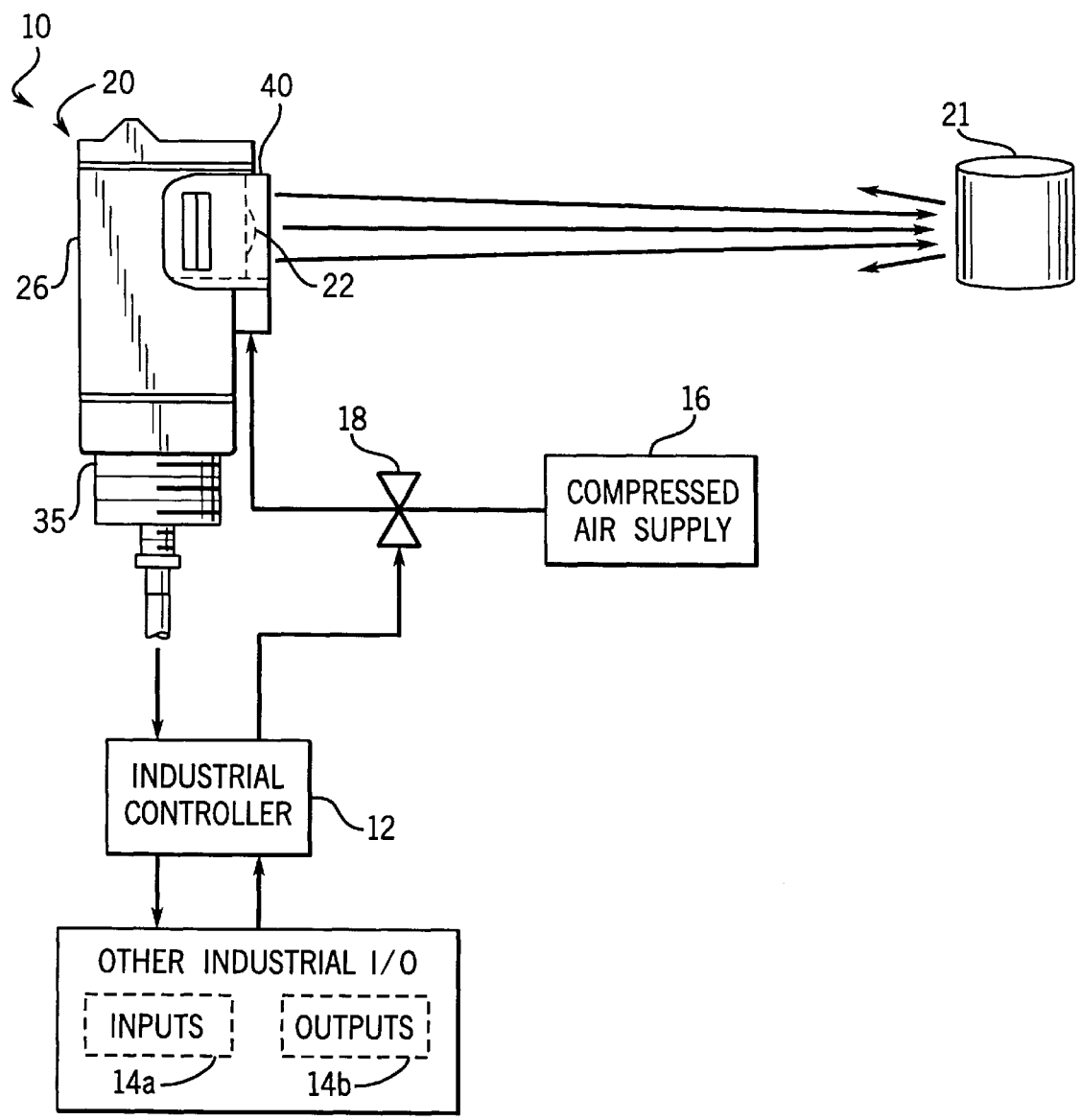
FIG. 1 illustrates an overview of an industrial control system which includes a photoelectric sensor having a dust removal attachment, in accordance with the present invention.

Referring now to FIG. 1, an industrial control system 10 includes an industrial controller (e.g., a programmable controller) 12 which examines and controls a plurality of inputs 14a and outputs 14b. Among the inputs received by the industrial controller 12 is an input from a photoelectric sensor 20, which provides an indication whether an object 21 is present within the field of view of the photoelectric sensor 20.

The photoelectric sensor 20 is assumed to be used in an environment in which dust or other types of dirt accumulate on a lens 22 of the photoelectric sensor 20. Herein, it is assumed that dust accumulates on the lens 22, it being understood that the invention is equally applicable to any other types of dirt (including residues, films, etc.) which could obstruct the lens 22.

To remove the dust from the lens 22 of the photoelectric sensor 20, an attachment 40 is provided which attaches to a housing 26 of the photoelectric sensor 20. The attachment 40 is connected to a fluid supply 16 (gaseous or liquidus), preferably a supply of compressed air. Air is preferred because it is inexpensive and because it allows the attachment 40 to be used with great frequency without having to worry about releasing undesirable chemicals into the environment. On the other hand, if a type of dirt other than dust must be removed, another type of fluid besides air may yield better results.

When the lens 22 of the photoelectric sensor 20 becomes obstructed by dust, the programmable controller 12 opens a valve 18 which causes a pulse of air to be directed toward the lens 22 of the photoelectric sensor 20. The pulse of air dislodges the dust, thereby restoring the photoelectric sensor 20 to an optimal level of operation.

Referring now also to FIGS. 2–8, the photoelectric sensor 20 is illustrated in greater detail. The photoelectric sensor 20 comprises the lens 22, the housing 26, and the attachment 40. The lens 22 includes a lens 24a for the source (not illustrated) and a lens 24b for the detector (not illustrated), respectively.

The housing 26 is a six-sided housing having a front side 28, right and left sides 30a and 30b, a lid 32 and bottom and back sides (not illustrated). Each of the sides 30a, 30b has a a fitting formed therein, preferably notch 34a, 34b. The front side 28 of the housing 26, which is the side of the housing 26 on which the lens 22 is disposed, is referred to as the face of the photoelectric sensor 20. The source and the detector are disposed in the housing 26 with the lens 24 being optically disposed between the light detector (and the light source) and the object 21. The lid 32 opens up to reveal a plurality of controls (not illustrated) for the photoelectric sensor 20. The housing 26 also includes a threaded fitting 35 used for mounting the photoelectric sensor 20.

The attachment 40 is not integrally formed with the housing 26 but rather simply attaches to the housing 26. The advantage of this approach is that it simplifies manufacturing. Further, many users of photoelectric sensors do not have a need for (and therefore do not wish to pay for) the cleaning device formed by the attachment 40. Providing the cleaning device in the form of attachment 40 permits the same housing 26 to be used both for photoelectric sensors which incorporate a cleaning device and those which do not incorporate a cleaning device.

Figure 2:
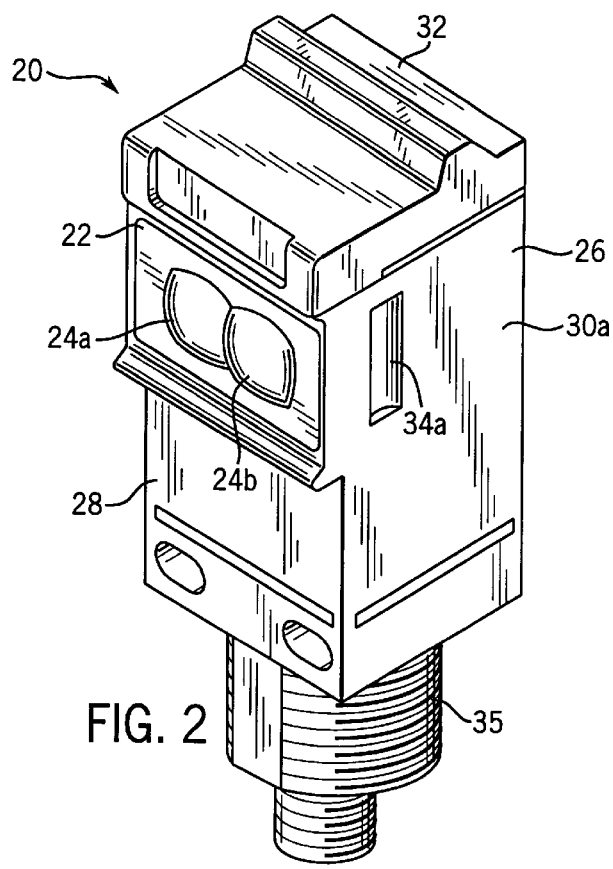
FIG. 2 illustrates a detailed view of the photoelectric sensor of FIG. 1 without the dust removal attachment, in accordance with the present invention.
Figure 3:
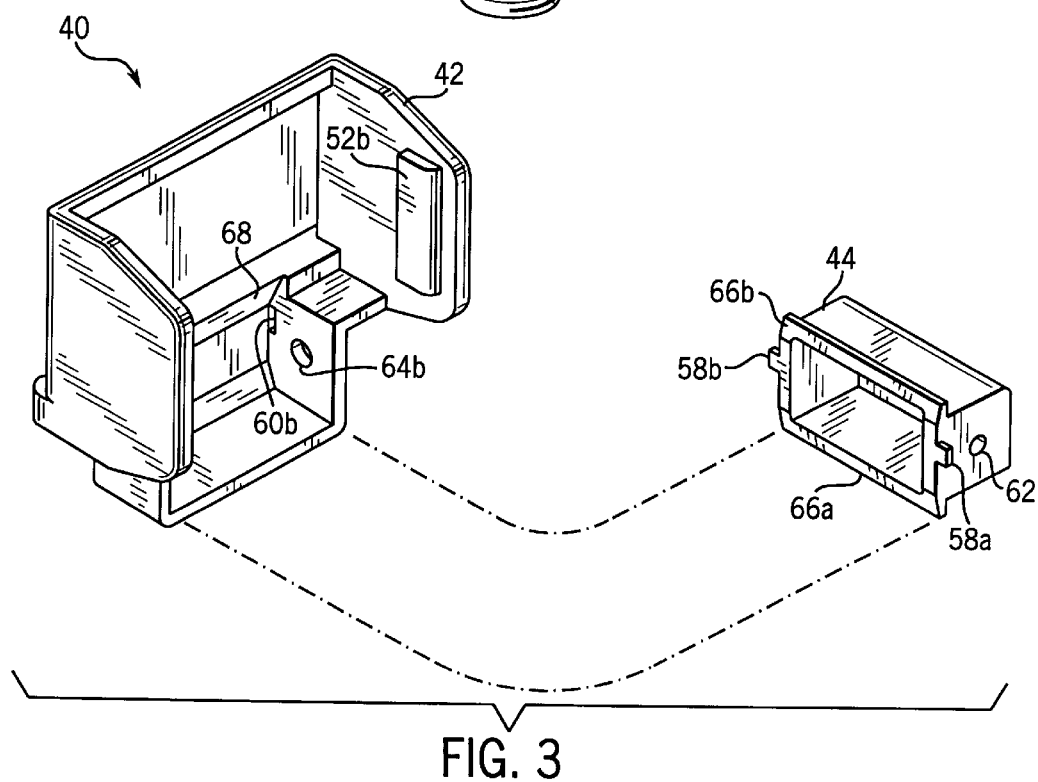
FIG. 3 illustrates a disassembled view of a principal section and an insert which form the dust removal attachment of FIG. 1, in accordance with the present invention.
Figure 4:
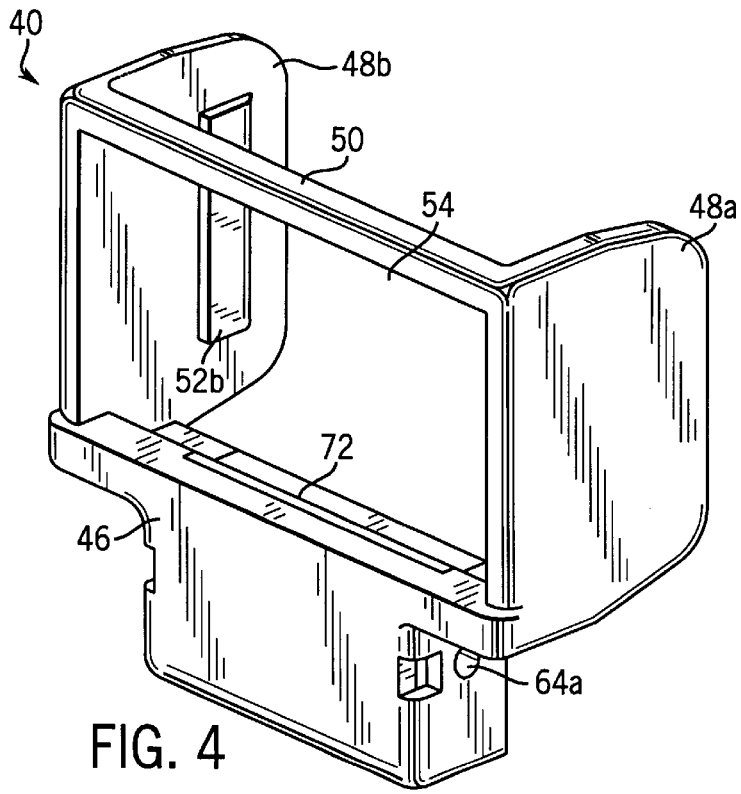
FIG. 4 illustrates an assembled view of the principal section and the insert which form the dust removal attachment of FIG. 1, in accordance with the present invention.
Figure 5:
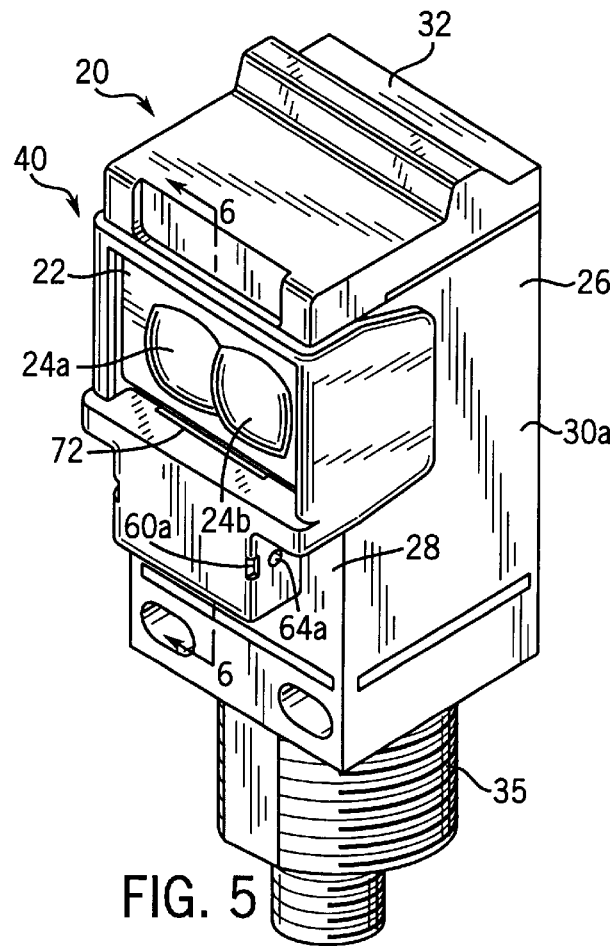
FIG. 5 illustrates a detailed view of the photoelectric sensor of FIG. 1 with the dust removal attachment, in accordance with the present invention.

From FIGS. 2 and 4, it can be seen that the lens 24 is mounted substantially directly to the housing 26 and, for example, is not mounted to the housing 26 by way of the attachment 40. Therefore, the lens 24 is mounted to the housing 26 even if the attachment 40 is not present (e.g., because it has been removed, or because it was never provided in the first place). Moreover, since the lens 24 is mounted to the housing 26 regardless whether the attachment 40 is present, the photoelectric sensor is usable without the attachment 40 (e.g., in situations where dust is not a problem).

The attachment 40 is preferably formed of plastic and comprises a principal section 42 and an insert section 44. Constructing the attachment 40 from two separate components in this manner facilitates fabrication of the attachment 40, because it enables injection molding to be used to form the components from plastic while still permitting an air chamber 56 to be formed within the attachment 40.

The principal section 42 further includes a base 46, right resilient and left retainer sections 48a and 48b, and a lateral support 50. The right and left retainers 48a and 48b are generally flat and planar and are generally parallel to each other as well as to the first and second sides of the housing 26. However, the right and left retainers 48a and 48b are generally perpendicular to the face 28 of the photoelectric sensor 20. The left and right retainers 48a and 48b include fittings, preferably ridges 52a and 52b, which engage the notches 34a and 34b so as to attach the attachment 40 to the sides 30a and 30b of the housing 26. The 52a and 52b thereby cooperate with the notches 34a and 34b to prevent removal of the attachment 40 from the housing 26 except through deformation of the right and left retainers 48a and 48b, and to thereby releasably attach the attachment 40 to the housing 26. Notably, the notches 34a and 34b and the ridges 52a and 52b are integrally formed with the housing 26 and the right and left retainers 48a and 48b, respectively, and the use of separate fasteners that are not integrally formed with the housing and the attachment (e.g., screws) is not required. A window 54 is defined by a top surface of the base 46, the right and left retainers 48a and 48b and the lateral support 50. The window 54 permits an unobstructed light path between the lens 22 and an object within the field of view of the photoelectric detector 20 (i.e., assuming the light path is not otherwise obstructed by dirt).

The base 46 and the insert 44 combine to form the air chamber 56. The front of the air chamber 56 is enclosed by the base 46, while the top and back of the air chamber 56 are enclosed by the insert 44. The remaining sides are enclosed by both the base 46 and the insert 44. The insert 44 has fittings (ridges 58a and 58b) which snap into fittings (ridges 60a and 60b) and which firmly secure the insert 44 within the base 46.

The insert 44 has a ⅛ NPT (national pipe tap) threaded hole 62 formed therein. The tapped hole 62 is of a standard size to facilitate connection with the compressed air supply 16 (see FIG. 1). The tapped hole 62 is accessible through one of two holes 64a, 64b formed in the base 46 of the attachment 40. Two holes 64a, 64b are provided so that the tapped hole 62 may appear on either the left or the right side of the base 46, as convenient, depending on how the insert 44 is placed within the base 46. This arrangement provides mounting flexibility, because a hose may be connected to the tapped hole 62 from either side of the photoelectric sensor 20, depending on which side is more accessible or convenient.

The insert has bottom and top lips 66a and 66b. The bottom lip 66a presses up firmly against the surface of the base 46 so as to form an essentially air-tight seal. The top lip 66b is spaced slightly from a corresponding lip 68 of the base 46. This arrangement causes a channel 70 to be formed which terminates with a slotted orifice 72 which serves as a fluid dispenser. The slotted orifice 72 is disposed adjacent to the lens 22, so that air dispensed from the slotted orifice 72 reaches the lens 22 with sufficient velocity to dislodge dust therefrom.

The lips 66a and 66b are angled such that air blows "back" (from a forward position to a rear position) and "up" (from a lower position to an upper position) towards the lens 22. This arrangement causes better distribution of the air over the surface of the lens 22 and therefore more effective dislodgement of dust from the lens 22. In the illustrated embodiment, it has been found that a lip having an angle in the range of about fifteen to thirty-five degrees (with respect to the plane in which the lens 22 is mounted) works particularly well.

The operation of the photoelectric sensor 20 is as follows. Dust accumulates on the lens 22 of the photoelectric sensor 20 as the factory operates and the photoelectric sensor 20 engages in normal sensing activities. Eventually, it is determined that the optical lens 22 is in need of cleaning. This step could be performed manually by an individual who visually inspects the lens 22 or who monitors the performance of the photoelectric sensor 20. Preferably, however, this step is performed automatically by the programmable controller 12. For example, a timer function could be initiated in the programmable controller 12 so that the programmable controller 12 recognizes when a predetermined amount of time has elapsed. Assuming dust accumulates on the lens 22 at a more or less constant rate, it can be assumed that the lens 22 is in need of cleaning after the predetermined amount of time has elapsed. An even more preferred approach is to have the programmable controller 12 monitor the build up of dust by monitoring the operating performance of the photoelectric sensor 20, such as by monitoring its operating margin.

When the programmable controller 12 determines that the lens 22 is in need of cleaning, the programmable controller 12 outputs a signal to the valve 18 which causes the valve to open and then close. This causes a pulse of air to be delivered to the photoelectric sensor 20 from the compressed air supply 16.

Figure 6:
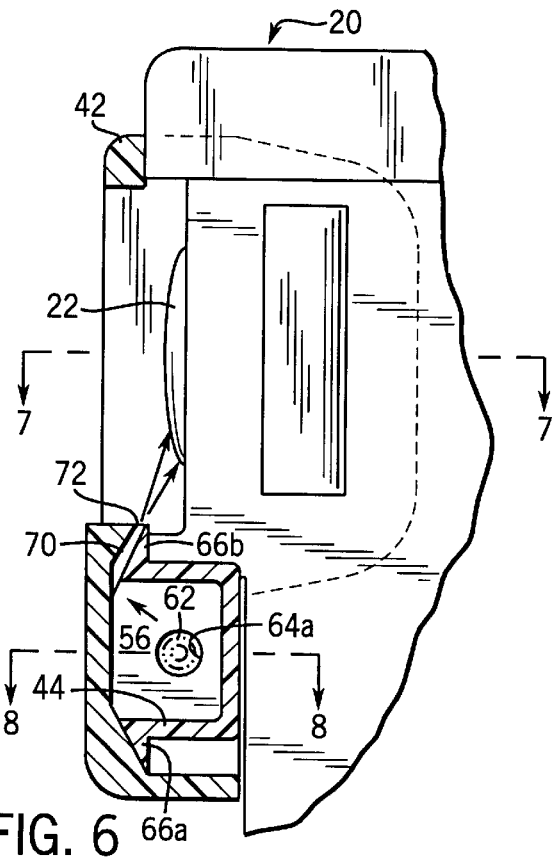
FIG. 6 illustrates a view taken along the lines 6—6 in FIG. 5.
Figure 7:
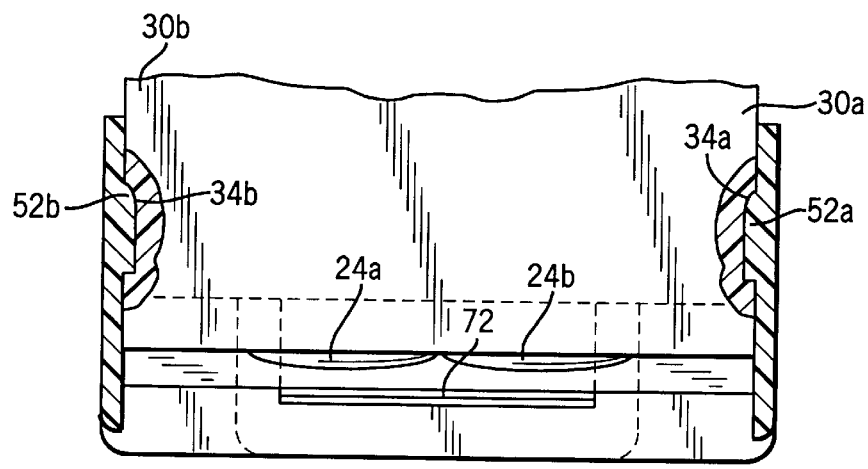
FIG. 7 illustrates a view taken along the lines 7—7 in FIG. 6.
Figure 8:
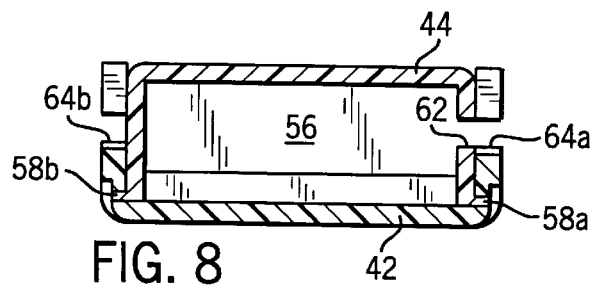
FIG. 8 illustrates a view taken along the lines 8—8 in FIG. 6.

At the photoelectric sensor 20, the pulse of air is received at the tapped hole 62. Since air is already present in the air chamber 56, and since the air chamber 56 is sealed except at the tapped hole 62 and the slotted orifice 72, the pulse of air is transmitted through the air chamber 56 and through the channel 70 and is dispensed from the slotted orifice 72. Upon exiting the slotted orifice 72, the pulse of air encounters the lens 22 and dislodges dust therefrom. This is shown in FIG. 6 by the three radially dispersed arrowheads of varying length.

Advantageously, the present invention provides a cleaning system which accommodates different possibilities for mounting a photoelectric sensor in different locations and orientations. The hose from the compressed air supply is brought directly to the photoelectric sensor which is already mounted, rather than to a separate piece of equipment which must be separately mounted. There is no need to separately determine a way to mount the cleaning device to nearby factory equipment, because the cleaning device is a part of the photoelectric sensor.

Moreover, the orientation of the photoelectric sensor is no longer important to the implementation of a cleaning system. Whether the sensor faces up, down, to the side, or a combination thereof is no longer important, because the orientation of the cleaning device changes as the orientation of the photoelectric sensor changes.

Furthermore, the present invention facilitates factory changes and upgrades. If the photoelectric sensor is moved from one location to another, the cleaning device moves too, because the cleaning device is a part of the photoelectric sensor. All that might be required is a longer hose to the fluid supply, which is easily provided. It is not necessary to determine a new way to mount the cleaning device to other factory equipment.

Additionally, the present invention can be used for different types of photoelectric sensors having different housing configurations. Although the cleaning device would have a different configuration for different types of photoelectric sensors having different housings, this design work can be accomplished by the manufacturer of the photoelectric sensor. The manufacturer is then able to provide a single solution for all users of the particular type of photoelectric sensor.

Finally, since the cleaning device is not integrally formed with the main housing but rather attaches to the sensor housing, the same sensor housing may be used for both for photoelectric sensors which incorporate a cleaning device and for those which do not incorporate a cleaning device. As a result, providing a cleaning device for those users who need the extra cleaning capability becomes more cost effective. The use of the same housing also promotes standardization.

Many changes and modifications may be made to the present invention without departing from the spirit thereof. The scope of these changes will become apparent from the appended claims.

I claim:

1. An industrial control system comprising:
   (A) a photoelectric sensor, said photoelectric sensor being constructed and arranged to provide an indication of whether an object is present within the field of view of said photoelectric sensor, said photoelectric sensor including
      (1) a light source, said light source emitting a beam of light,
      (2) a light detector, said light detector receiving said beam of light from said light source as a function of the presence of said object within the field of view of said photoelectric sensor, the reception of said beam of light at said light detector permitting said photoelectric sensor to provide said indication of whether said object is present within said field of view of said photoelectric sensor, (3) an optical lens, said optical lens being optically disposed between said light detector and said object, (4) a housing, said housing having first and second sides with fittings disposed thereon that are integrally formed with said housing, said housing having a third side with said optical lens disposed thereon so as to define a face of said photoelectric sensor, and said housing having said light detector disposed therein, and (5) a cleaning device which removes dust from said optical lens, said cleaning device being an attachment which is non-integrally formed with said housing and which attaches to said housing, said attachment including (a) a principal section further including
      (i) a base, said base having fittings disposed thereon that are integrally formed with said base,
      (ii) a lateral support, and
      (iii) first and second resilient retainers, said first and second retainers having fittings disposed thereon that are integrally formed with said first and second retainers, said first and second retainers being generally flat and planar, said first and second retainers being generally parallel to each other and to said first and second sides of said housing, and said first and second retainers being generally perpendicular to said face of said photoelectric sensor,
   wherein said base, said lateral support and said first and second retainers define a window which permits an unobstructed field of view for said photoelectric sensor, and
   wherein said fittings disposed on said first and second retainers cooperate with said fittings disposed on said first and second sides of said housing to prevent removal of said cleaning device attachment from said housing except through deformation of said first and second retainers and thereby to releasably attach said cleaning device attachment to said housing without the use of separate fasteners that are not integrally formed with said first and second retainers and said housing, and
   (b) an insert which is inserted into said base of said principal section, said insert having fittings disposed thereon that are integrally formed with said insert, and
   wherein said fittings disposed on said insert cooperate with said fittings disposed on said base to hold said insert within said base without the use of separate fasteners that are not integrally formed with said base and said insert,
   wherein said insert and said principal section combine to form an air chamber and an air dispenser, said air chamber being coupled to a source of compressed air, said air dispenser being in fluid communication with said air chamber, and said air dispenser comprising a slotted orifice formed between a lip of said base and a lip of said insert; and (B) an industrial controller, said industrial controller controlling a plurality of output devices based on inputs received from a plurality of input devices, said industrial controller being coupled to said photoelectric sensor such that one of said plurality of input devices is said photoelectric sensor, said industrial controller also being coupled to a valve which controls the flow of air from said source of compressed air to said cleaning device attachment, said industrial controller thereby controlling the cleaning of said optical lens; and wherein said optical lens is mounted substantially directly to said housing and is not mounted to said housing by way of said cleaning device attachment, such that said optical lens is mounted to said housing even if said cleaning device attachment is removed, and such that said photoelectric sensor is usable with and without said cleaning device attachment; and wherein said cleaning device attachment attaches to said housing such that said air dispenser is disposed adjacent said optical lens and is operative to dispense air on said optical lens to dislodge said dust from said optical lens.

2. An industrial control system according to claim 1, wherein said lip of said principal section and said lip of said insert are angled, and wherein an angle between the plane in which said lens is mounted and the plane defined by one of said angled lips is approximately in the range of fifteen to thirty-five degrees.

3. An industrial control system according to claim 1, wherein said fittings disposed on said first and second sides of said housing and said fittings disposed on said first and second retainers are all snap fittings.

4. An industrial control system according to claim 3, wherein said snap fittings disposed on said first and second sides of said housing comprise first and second notches that extend parallel to said face of said photoelectric sensor, and wherein said snap fittings disposed on said first and second retainers comprise first and second ridges that extend parallel to said face of said photoelectric sensor.

5. An industrial control system according to claim 1, wherein said fittings disposed on said insert and said fittings disposed on said base are all snap fittings.

6. An industrial control system according to claim 5, wherein said snap fittings disposed on said insert comprise ridges, and wherein said snap fittings disposed on said base comprise notches.

7. An industrial control system according to claim 1, wherein said light source is also contained in said housing.

8. An industrial control system comprising:

(A) an industrial controller, said industrial controller controlling a plurality of output devices based on inputs received from a plurality of input devices;

(B) a photoelectric sensor, said photoelectric sensor being one of said plurality of input devices, said photoelectric sensor providing said industrial controller with an input that indicates whether an object is present within the field of view of said photoelectric sensor, said photoelectric sensor including (1) a light source, said light source emitting a beam of light,
   (2) a light detector, said light detector receiving said beam of light from said light source as a function of the presence of said object within said field of view of said photoelectric sensor, the reception of said beam of light at said light detector permitting said photoelectric sensor to provide said industrial controller with said input that indicates whether said object is present within said field of view of said photoelectric sensor, (3) a housing, said housing having said light detector disposed therein, (4) an optical lens, said optical lens being optically disposed between said light detector and said object, and said optical lens being mounted to said housing, (5) a cleaning device that removes contaminants from said optical lens of said photoelectric sensor, said cleaning device being an attachment which is non-integrally formed with said housing, said cleaning device attachment including (a) an input which receives a cleaner in a gaseous state, and (b) dispenser which dispenses said cleaner, said dispenser being disposed adjacent said optical lens, and said dispenser dispensing said cleaner so as to dislodge said contaminants from said optical lens; and wherein said optical lens is mounted substantially directly to said housing and is not mounted to said housing by way of said cleaning device attachment, such that said optical lens is mounted to said housing even if said cleaning device attachment is removed, and such that said photoelectric sensor is usable with and without said cleaning device attachment; and wherein said cleaning device attachment attaches to said housing such that said dispenser is disposed adjacent said optical lens and is operative to dispense said cleaner on said optical lens to dislodge said contaminants from said optical lens.

9. An industrial control system according to claim 8, wherein said attachment further includes first and second retainers that are generally flat and planar, said first and second retainers being generally parallel to each other and to first and second sides of said housing, and said first retainer attaching said attachment to said first side of said housing and said second retainer attaching said attachment to said second side of said housing.

10. An industrial control system according to claim 8, wherein said housing has fittings disposed thereon, and wherein said attachment further includes first and second resilient retainers, said first retainer attaching said attachment to said first side of said housing and said second retainer attaching said attachment to said second side of said housing, said first and second retainers having fittings disposed thereon, said fittings disposed on said first and second retainers cooperating with said fittings disposed on said housing to prevent removal of said cleaning device attachment from said housing except through deformation of said first and second retainers and thereby to releasably attach said cleaning device attachment to said housing.

11. An industrial control system according to claim 10, wherein said fittings disposed on said first and second sides of said housing and said fittings disposed on said first and second retainers are all snap fittings.

12. An industrial control system according to claim 11, wherein said snap fittings disposed on said first and second sides of said housing comprise first and second notches that extend parallel to a side of said photoelectric sensor on which said optical lens is disposed, and wherein said snap fittings disposed on said first and second retainers comprise first and second ridges that extend parallel to said side of said photoelectric sensor on which said optical lens is disposed.

13. An industrial control system according to claim 11, wherein said snap fittings disposed on said first and second sides of said housing are integrally formed with said housing and wherein said snap fittings disposed on said first and second retainers are integrally formed with said first and second retainers.

14. An industrial control system according to claim 8, wherein said attachment is formed of a plurality of plastic sections including a first plastic section and a second plastic section, and wherein said dispenser is formed of a slotted orifice formed between a lip of said first plastic section and a lip of said second plastic section.

15. An industrial control system according to claim 14, wherein said first and second plastic sections each include fittings that attach said first and second plastic sections to each other, and wherein said fittings disposed on said first and second plastic sections are all snap fittings.

16. An industrial control system according to claim 15, wherein said snap fittings disposed on said first plastic section comprise ridges, and wherein said snap fittings disposed on said second plastic section comprise notches.

17. An industrial control system according to claim 15, wherein said snap fittings disposed on said first plastic section are integrally formed with said first plastic section, and wherein said snap fittings disposed on said second plastic section are integrally formed with said second plastic section.

18. An industrial control system according to claim 14, wherein said lip of said first plastic section and said lip of said second plastic section are angled, and wherein an angle between the plane in which said optical lens is mounted and the plane defined by one of said angled lips is approximately in the range of fifteen to thirty-five degrees.

19. An industrial control system according to claim 18, wherein said light source is also contained in said housing.

20. An industrial control system according to claim 19, wherein said cleaner includes air.

* * * * *